(12) United States Patent
Siciliano

(10) Patent No.: US 12,415,059 B2
(45) Date of Patent: Sep. 16, 2025

(54) DEVICE FOR OFFSET WIRELESS TATTOO BATTERY PACK AND METHODS OF USE

(71) Applicant: FK IRONS INC., Doral, FL (US)

(72) Inventor: Gaston Siciliano, Doral, FL (US)

(73) Assignee: FK IRONS INC., Doral, FL (US)

( * ) Notice: Subject to any disclaimer, the term of this patent is extended or adjusted under 35 U.S.C. 154(b) by 688 days.

(21) Appl. No.: 17/191,523

(22) Filed: Mar. 3, 2021

(65) Prior Publication Data

US 2021/0402162 A1    Dec. 30, 2021

Related U.S. Application Data

(60) Provisional application No. 62/984,414, filed on Mar. 3, 2020.

(51) Int. Cl.
*A61M 37/00* (2006.01)
*H02J 7/00* (2006.01)

(52) U.S. Cl.
CPC ....... *A61M 37/0076* (2013.01); *H02J 7/0042* (2013.01); *H02J 7/0048* (2020.01); *H02J 7/0063* (2013.01); *A61M 2205/502* (2013.01); *A61M 2205/584* (2013.01); *A61M 2205/8206* (2013.01); *A61M 2205/8237* (2013.01)

(58) Field of Classification Search
CPC ...... H02J 7/0063; H02J 7/0042; H02J 7/0044; H02J 7/0045; H02J 7/0047; H02J 7/0048; H02J 7/0049; H02J 7/005; H02J 7/007; A61M 37/0076; A61M 2205/8206; A61M 2205/502; A61M 2205/584; A61M 2205/82; A61M 2205/8237; A01K 11/00; A01K 11/005

See application file for complete search history.

(56) References Cited

U.S. PATENT DOCUMENTS

| | | |
|---|---|---|
| 4,204,438 A | 5/1980 | Binaris |
| 4,914,988 A | 4/1990 | Chang |
| 5,165,488 A | 11/1992 | Liu |

(Continued)

FOREIGN PATENT DOCUMENTS

| | | |
|---|---|---|
| AU | 2019359618 | 5/2020 |
| CA | 1283458 | 4/1991 |

(Continued)

OTHER PUBLICATIONS facebook.com, "Battery Pack For Wireless Tattooing," Jan. 18, 2019, 10 pages.

(Continued)

*Primary Examiner* — Robert A Lynch
(74) *Attorney, Agent, or Firm* — Akerman LLP; Peter A. Chiabotti

(57) ABSTRACT

An independently operable offset wireless tattoo machine battery pack is disclosed. The battery pack is offset relative to a tattoo machine power interface such that the center of gravity of the battery pack is longitudinally closer to the center of gravity of the tattoo machine than is the power interface. The offset wireless tattoo machine battery pack may include electronic circuitry that controls and operates a tattoo machine independent of any separate control unit, providing a unified wireless standalone tattoo machine.

12 Claims, 11 Drawing Sheets

(56) References Cited

U.S. PATENT DOCUMENTS

| | | | |
|---|---|---|---|
| 6,392,460 B1 * | 5/2002 | Vail | G05B 5/01 |
| | | | 327/172 |
| 6,550,356 B1 | 4/2003 | Underwood | |
| 7,393,114 B2 | 7/2008 | Devlin | |
| 8,171,825 B1 * | 5/2012 | Adams | H02K 33/04 |
| | | | 606/186 |
| 8,228,666 B2 | 7/2012 | Rickard | |
| 8,393,249 B2 | 3/2013 | Godoy | |
| D703,825 S | 4/2014 | Barrett | |
| 9,433,767 B2 | 9/2016 | Colton et al. | |
| 9,452,281 B2 | 9/2016 | Chan | |
| 9,662,483 B2 | 5/2017 | Siciliano | |
| 10,052,469 B2 | 8/2018 | Chan et al. | |
| 10,220,195 B2 | 3/2019 | O'Brien | |
| 10,220,196 B2 | 3/2019 | Johansson | |
| 10,226,611 B1 | 3/2019 | Collias | |
| 10,471,246 B1 * | 11/2019 | Lipscomb | H02J 7/00 |
| 10,898,704 B2 | 1/2021 | Vescovi | |
| D910,846 S | 2/2021 | Siciliano | |
| 2004/0230157 A1 | 11/2004 | Perry | |
| 2005/0090851 A1 | 4/2005 | Devlin | |
| 2008/0300615 A1 | 12/2008 | Colton | |
| 2009/0280667 A1 * | 11/2009 | Pallino | H01R 13/22 |
| | | | 439/269.1 |
| 2010/0072827 A1 | 3/2010 | Norstrom | |
| 2010/0241151 A1 | 9/2010 | Rickard | |
| 2011/0288575 A1 * | 11/2011 | Colton | A61M 37/0076 |
| | | | 606/185 |
| 2012/0024114 A1 | 2/2012 | Vazquez | |
| 2012/0112687 A1 * | 5/2012 | Houser | H01M 50/247 |
| | | | 340/635 |
| 2013/0096599 A1 | 4/2013 | Colton | |
| 2014/0094837 A1 | 4/2014 | Danenberg | |
| 2014/0220403 A1 | 8/2014 | Ro | |
| 2014/0324089 A1 | 10/2014 | Chan | |
| 2015/0202420 A1 | 7/2015 | Miller | |
| 2015/0352346 A1 | 12/2015 | Webb | |
| 2015/0367118 A1 | 12/2015 | Scherkowski | |
| 2016/0074645 A1 | 3/2016 | Siciliano | |
| 2016/0121093 A1 | 5/2016 | Fan | |
| 2016/0172722 A1 * | 6/2016 | Rejman | H01M 10/425 |
| | | | 429/7 |
| 2016/0263365 A1 | 9/2016 | Smith | |
| 2017/0007814 A1 | 1/2017 | Chan | |
| 2017/0021154 A1 * | 1/2017 | Johansson | A61M 37/0076 |
| 2017/0157382 A1 | 6/2017 | Siciliano | |
| 2017/0173319 A1 | 6/2017 | McGuire | |
| 2018/0000419 A1 | 1/2018 | Rassman | |
| 2018/0013175 A1 | 1/2018 | Liu | |
| 2018/0043146 A1 | 2/2018 | Vescovi | |
| 2018/0056054 A1 | 3/2018 | Siciliano | |
| 2018/0056055 A1 | 3/2018 | Rutherford | |
| 2018/0200035 A1 | 7/2018 | Gagliano | |
| 2018/0369553 A1 | 12/2018 | Siciliano | |
| 2019/0053465 A1 | 2/2019 | Knight | |
| 2020/0038158 A1 | 2/2020 | Gagliano | |
| 2020/0114137 A1 | 4/2020 | Siciliano | |
| 2020/0306519 A1 | 10/2020 | Smead et al. | |

FOREIGN PATENT DOCUMENTS

| | | |
|---|---|---|
| CA | 2412681 | 4/2007 |
| CA | 2678952 | 7/2011 |
| CA | 3027165 | 12/2017 |
| CH | 704096 | 5/2012 |
| CN | 2894616 | 5/2007 |
| CN | 201775864 | 3/2011 |
| CN | 202161682 | 3/2012 |
| CN | 202173684 | 3/2012 |
| CN | 202396478 | 8/2012 |
| CN | 302423215 | 5/2013 |
| CN | 302440966 | 5/2013 |
| CN | 302873288 | 7/2014 |
| CN | 204379980 | 6/2015 |
| CN | 204521979 | 8/2015 |
| CN | 303520153 | 12/2015 |
| CN | 303627771 | 3/2016 |
| CN | 303987311 | 12/2016 |
| CN | 106492344 | 3/2017 |
| CN | 106730312 | 5/2017 |
| CN | 106805951 | 6/2017 |
| CN | 206424423 | 8/2017 |
| CN | 107508966 | 12/2017 |
| CN | 206792803 | 12/2017 |
| CN | 206852920 | 1/2018 |
| CN | 206924246 | 1/2018 |
| CN | 206924247 | 1/2018 |
| CN | 107952197 | 4/2018 |
| CN | 304577923 | 4/2018 |
| CN | 108211104 | 6/2018 |
| CN | 304746903 | 7/2018 |
| CN | 107146970 | 8/2018 |
| CN | 305086769 | 3/2019 |
| CN | 305154130 | 5/2019 |
| CN | 305172441 | 5/2019 |
| CN | 210114742 | 2/2020 |
| EP | 1872823 | 1/2008 |
| EP | 1882491 | 10/2009 |
| EP | 2944349 | 11/2015 |
| EP | 2954927 | 12/2015 |
| EP | 3482793 | 5/2019 |
| ES | 1195334 | 10/2017 |
| GB | 2567804 | 5/2019 |
| JP | 3126886 | 11/2006 |
| JP | 6242956 | 12/2017 |
| KR | 20170129685 | 11/2017 |
| KR | 1020190045900 | 5/2019 |
| SG | 195416 | 12/2013 |
| WO | 2008002383 | 1/2008 |
| WO | 2008146294 | 12/2008 |
| WO | 2011163134 | 12/2011 |
| WO | 2015094042 | 6/2015 |
| WO | 2015156715 | 10/2015 |
| WO | 2017178070 | 10/2017 |
| WO | 2017189606 | 11/2017 |
| WO | 2017194336 | 11/2017 |
| WO | 2019106552 | 6/2019 |
| WO | 2019106553 | 6/2019 |
| WO | 2021127721 | 7/2021 |

OTHER PUBLICATIONS

Webarchive.org, "Unchained Battery Operated," dated Jan. 21, 2015, 1 page.

Instagram, "FK Irons Spektra Xion," dated Jun. 2018, 3 pages.

Patent Cooperation Treaty, "International Search Report" issued in International Patent Application No. PCT/US21/20730, dated May 24, 2021; document of 14 pages.

Maxon Motors, "Inked to precision," dated Jan. 27, 2015, document of 3 pages.

Ink Machines, "Manual for TPS-5OO," dated May 25, 2018, document of 39 pages.

Maxon Motors, "Driven", dated Feb. 2014, document of 7 pages.

* cited by examiner

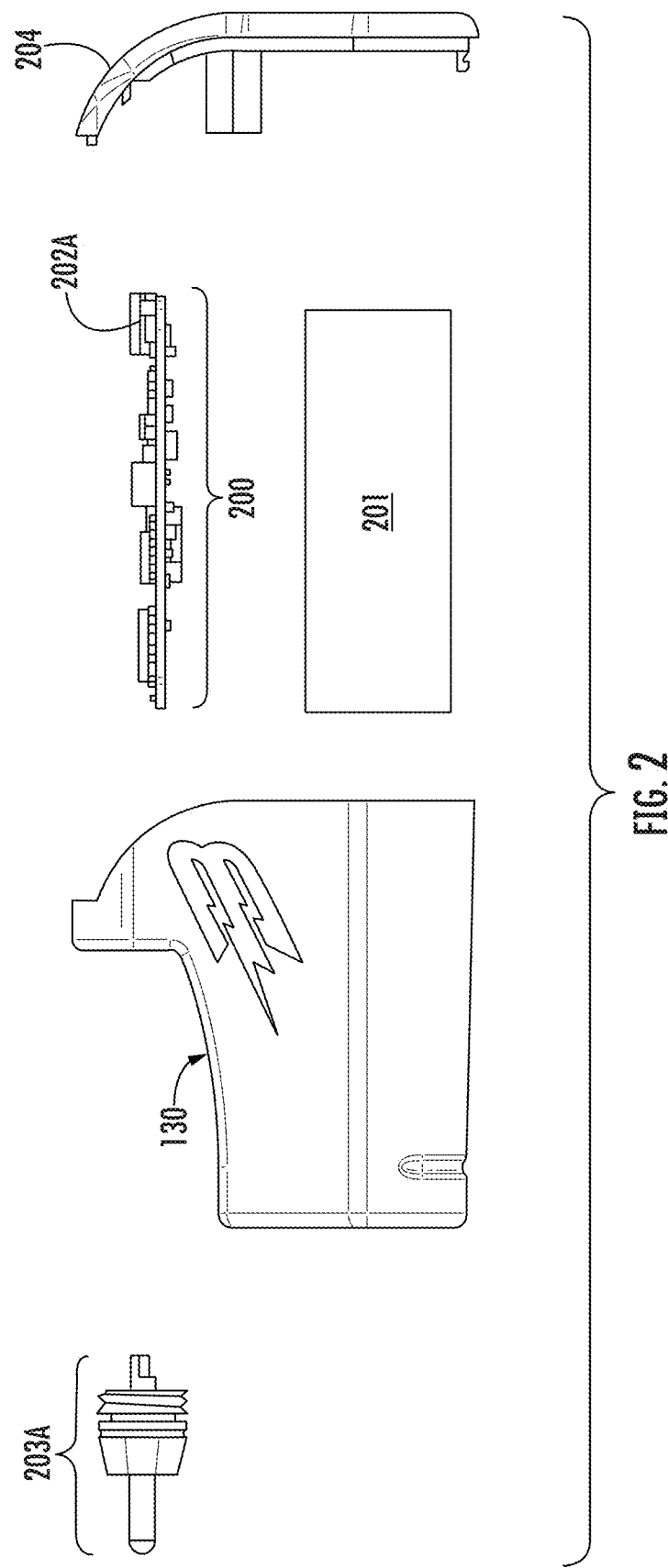

PANEL FRONT VIEW

CIRCUIT FRONT VIEW

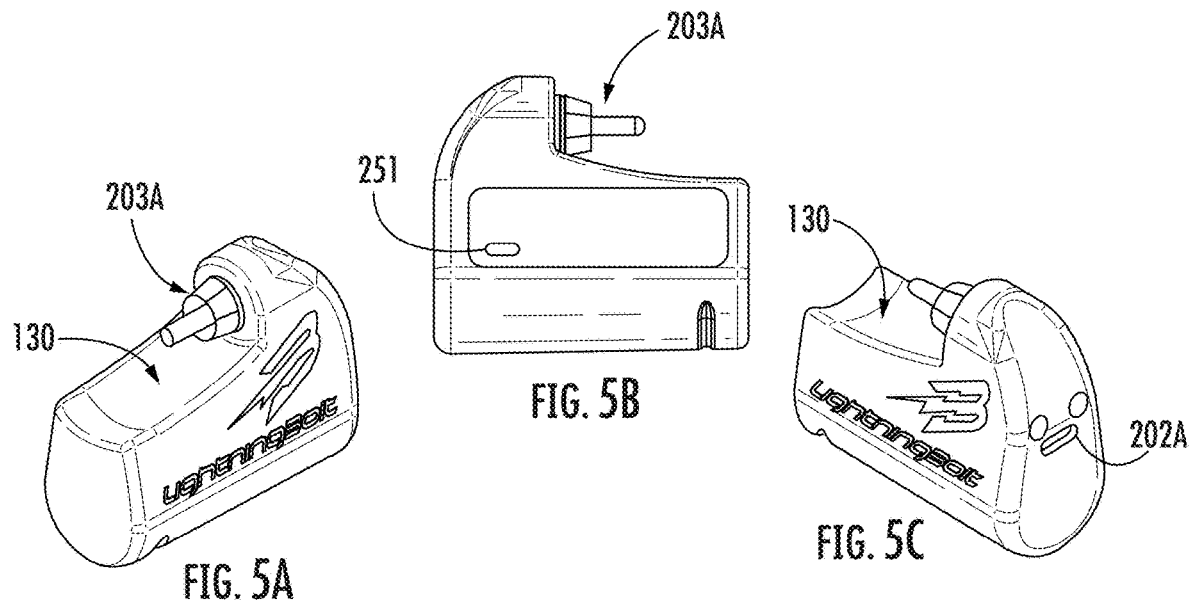
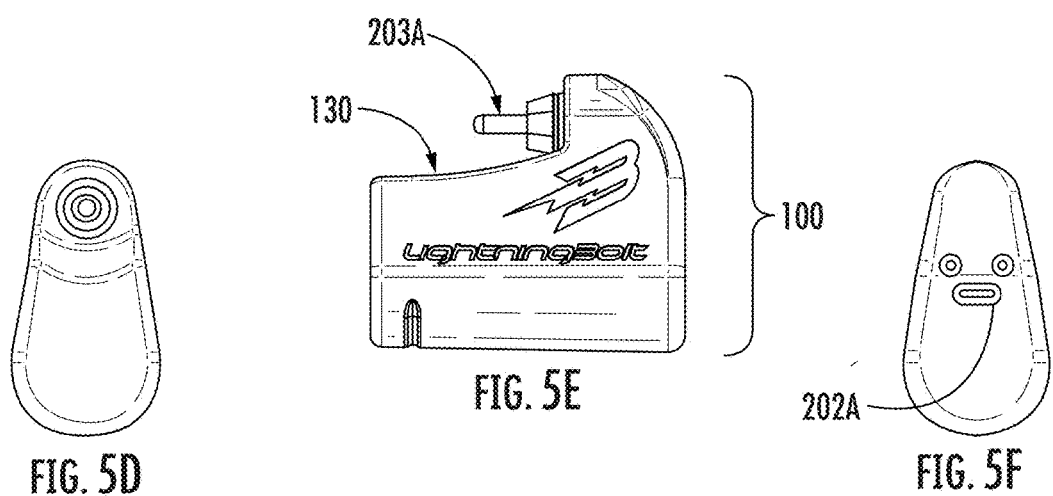
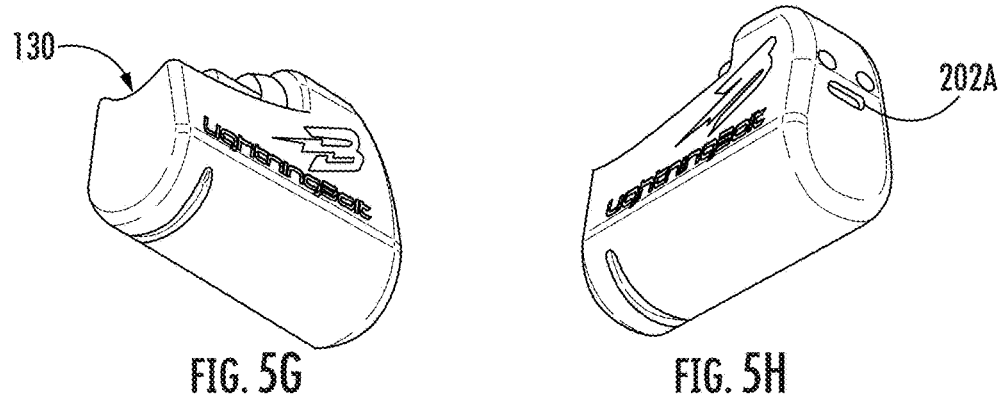

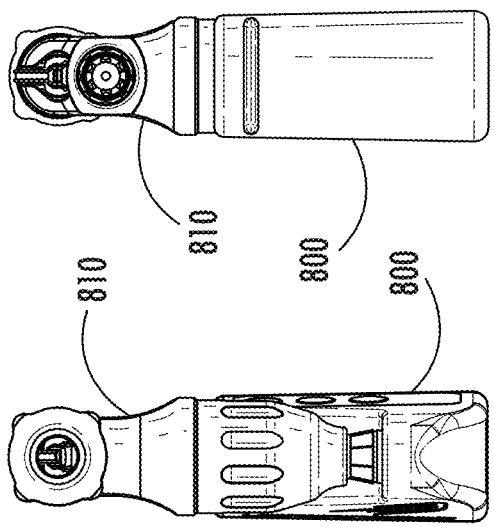
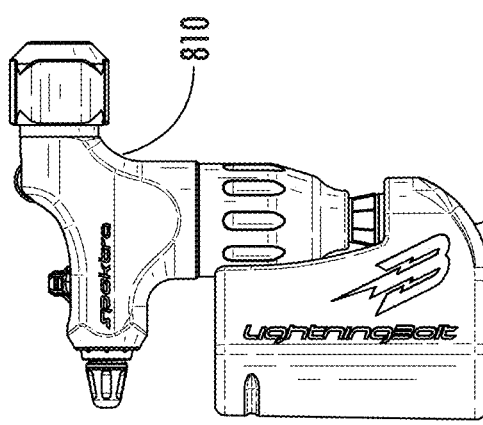
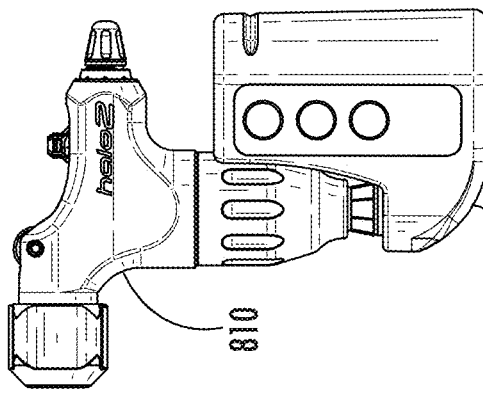
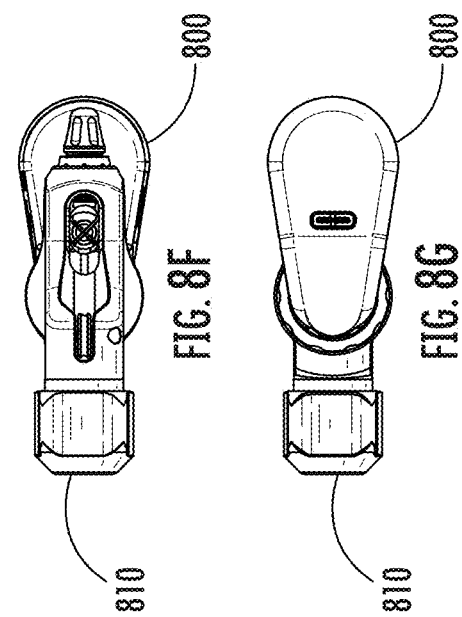
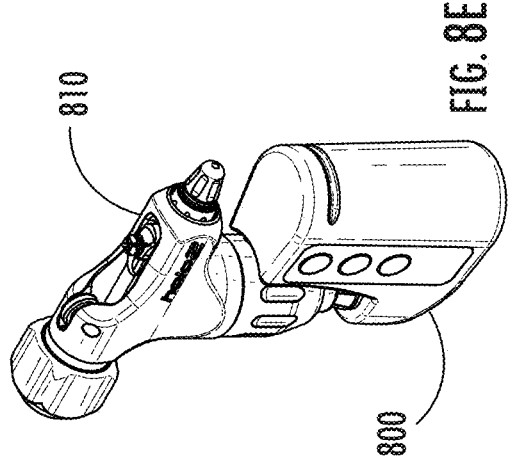

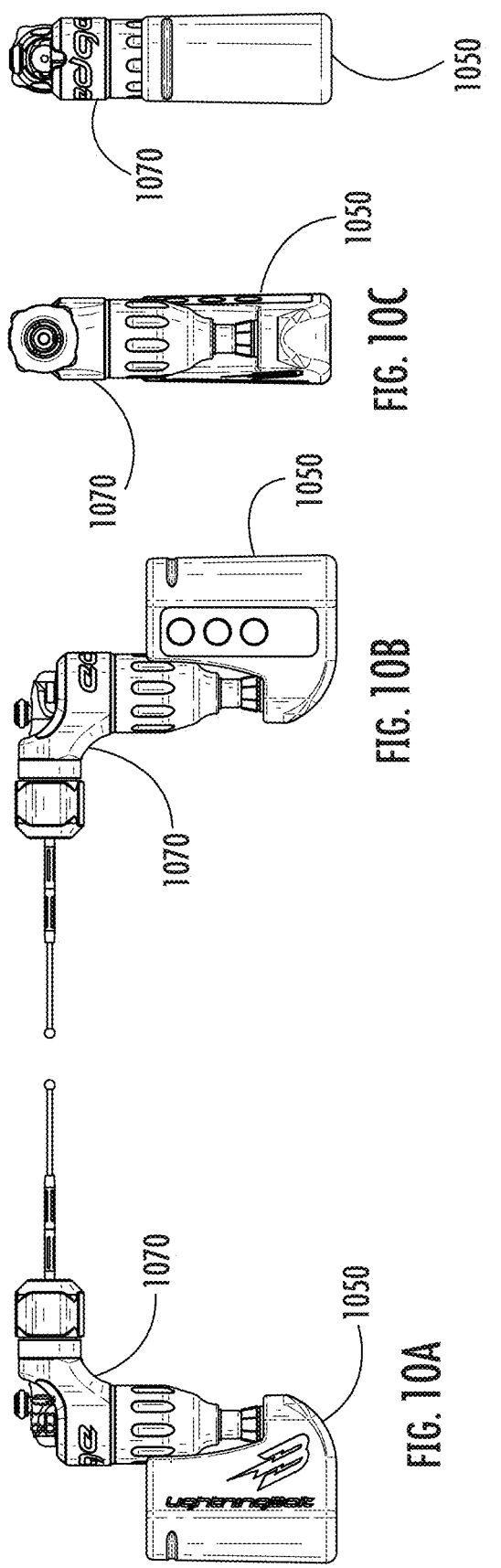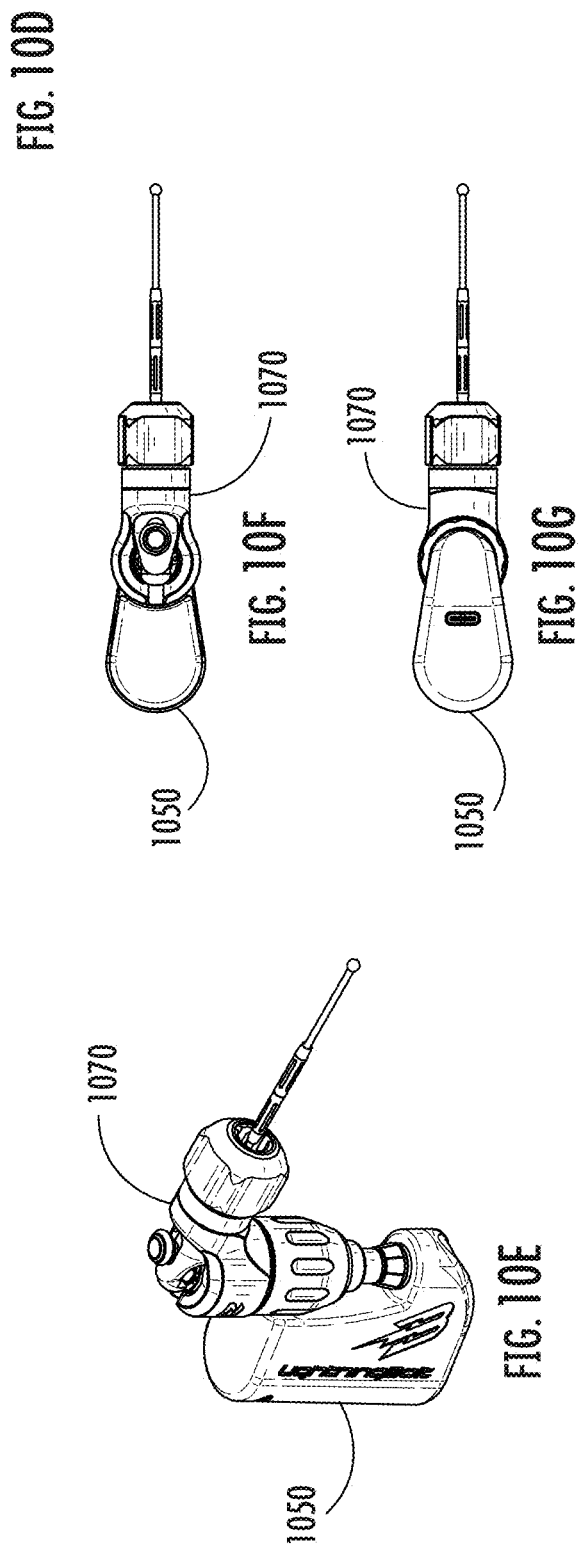

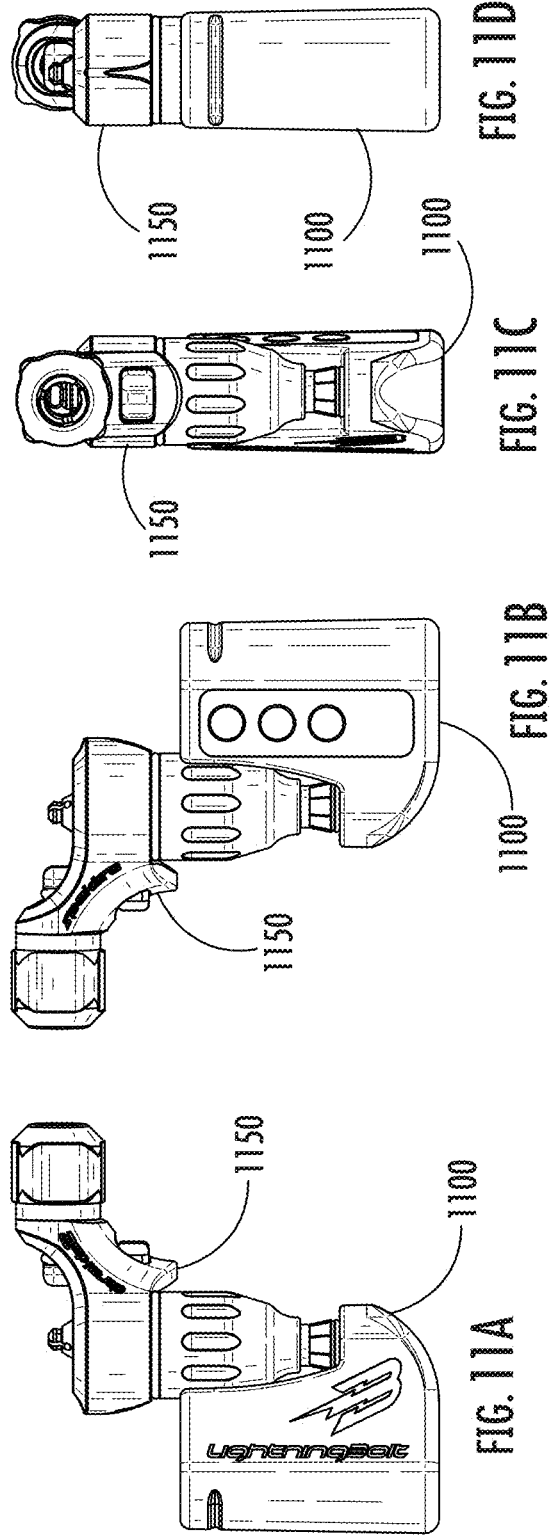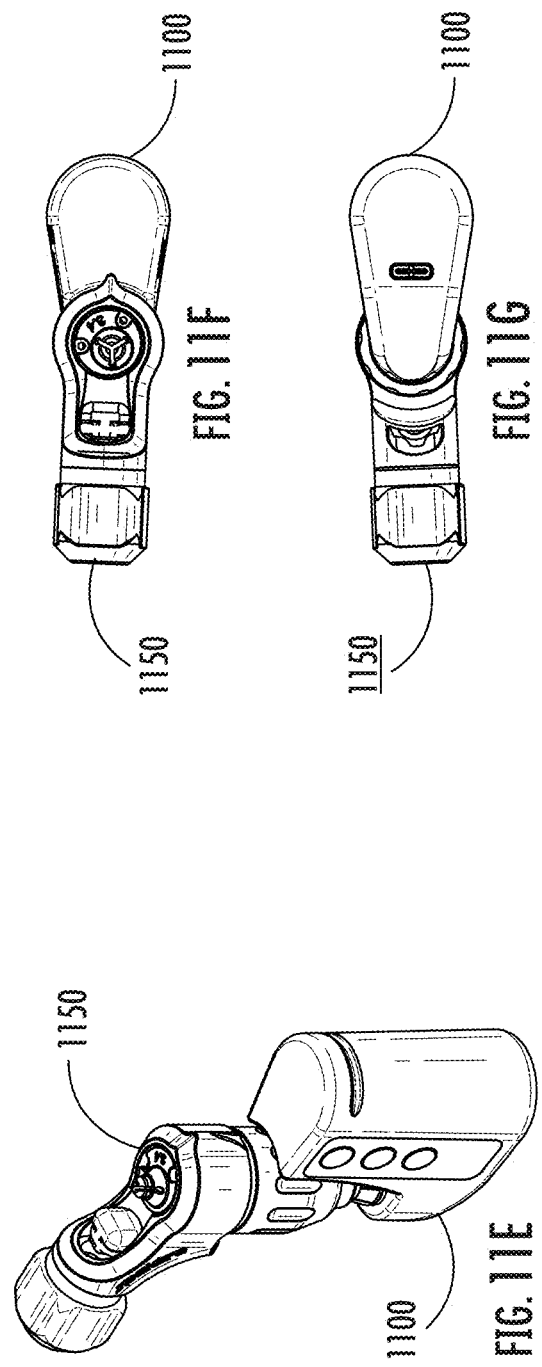

DEVICE FOR OFFSET WIRELESS TATTOO BATTERY PACK AND METHODS OF USE

CROSS REFERENCE TO RELATED APPLICATIONS

This application claims the benefit of U.S. Provisional Application No. 62/984,414, filed Mar. 3, 2020, the disclosure of which is hereby incorporated by reference in its entirety.

FIELD OF THE DISCLOSURE

The present disclosure generally relates to handheld needling devices and battery pack technologies, and more particularly to tattoo machines, permanent makeup machines, microneedling machines, and offset wireless battery packs.

BACKGROUND OF THE DISCLOSURE

Needling devices have continued to decrease in size and complexity. Tattoo machines in particular have become more pen-like such that the device fits more comfortably in a user's hand and is manipulable by fingertip. Power has traditionally been supplied to such devices by wire, thus limiting an artist's freedom. Wireless battery packs have been developed to supply power to needling machines, but the added weight increases user fatigue, and decreases how long an artist can utilize the device.

Needling machines, without a power source attached to them, have a center of mass inherently defined by the machine's materials and configuration. Wireless power sources, as a separate component from the needling machine, have their own center of mass defined by their own materials and geometry. When a needling machine is combined with a wireless battery pack, the combination machine plus battery pack is then characterized by an overall combined center of mass. Where the center of mass of the combination is more distant from the artist's hand, greater torque results at the front grip portion of the needling machine, thus increasing user fatigue.

While certain aspects of conventional technologies have been discussed to facilitate disclosure of the disclosure, Applicant in no way disclaims these technical aspects, and it is contemplated that the claimed disclosure may encompass one or more of the conventional technical aspects discussed herein.

In this specification where a document, act, or item of knowledge is referred to or discussed, that reference or discussion is not an admission that the document, act, or item of knowledge or any combination thereof was at the priority date, publicly available, known to the public, part of common general knowledge, or otherwise constitutes prior art under the applicable statutory provision; or is known to be relevant to an attempt to solve any problem with which this specification is concerned.

BRIEF SUMMARY OF THE DISCLOSURE

The following presents a simplified summary of the disclosure in order to provide a basic understanding of some aspects of the disclosure. This summary is not an extensive overview of the disclosure. It is intended neither to identify key or critical elements of the disclosure nor to delineate the scope of the disclosure. A purpose is to present some concepts of the disclosure, in accordance with the disclosure, in a simplified form as a prelude to the more detailed description presented later.

In one embodiment, an offset wireless battery pack is disclosed for use with a needling or tattoo machine.

In another embodiment of the disclosure, an offset wireless battery pack is provided which includes a housing, one or more battery cells, a machine power interface for delivering direct current voltage to a needling machine, a charging interface, and electronic circuitry in electrical communication with the one or more battery cells, the machine power interface, and the machine charging interface. In certain embodiments, the electronic circuitry may include a power controller, a processor, a memory, an input button, and a light emitting diode. The housing may have a main body portion and a machine mating portion. The main body portion may be dimensioned to house the battery cells and the electronic circuitry of the wireless battery pack. The machine mating portion of the housing may be positioned on a machine-facing side of the main body portion such that the machine power interface is offset from the main body portion. In this way, the offset wireless battery pack, when it is mated to a needling machine, is at an offset distance from the needling machine.

In another embodiment of the disclosure, an offset wireless battery pack kit is disclosed, which includes a needling machine with a cartridge end, and an input end, and an exterior machine profile, and an offset wireless battery pack having machine mating portion and a machine power interface. The machine mating portion is dimensioned to correspond to a portion of the exterior machine profile such that when the offset wireless battery pack is operatively connected to the needling machine, the offset wireless battery pack sits alongside the needling machine.

A further embodiment comprises an offset wireless battery pack device, which includes one or more battery cells, a machine power interface, a charging interface, electronic circuitry, and a housing. The housing has an exterior, an interior, and a machine mating portion. The interior of the housing is dimensioned to house the one or more battery cells and electronic circuitry. The combined battery cells, electronic circuitry, and interior define a main body portion of the housing. The main body portion has a center of mass. The machine mating portion may be positioned at a distance from the center of mass such that the center of mass is offset a distance from the needling machine when the offset wireless battery pack is mated to a needling machine.

Embodiments of the present disclosure may include components manufactured from various materials based upon the contemplated use. For embodiments that are contemplated for human use, materials that are durable, cleanable or autoclavable, and sanitary are contemplated to be within the scope of the present disclosure. By way of example and not limitation, materials may be stainless steel, anodized aluminum, and/or polycarbonates.

The present disclosure may address one or more of the problems and deficiencies of currently existing technology as discussed above. However, it is contemplated that the disclosure may prove useful in addressing other problems and deficiencies in a number of technical areas. Therefore, the claimed disclosure should not necessarily be construed as limited to addressing any of the particular problems or deficiencies discussed herein.

The following description and the annexed drawings set forth certain illustrative aspects of the disclosure. These aspects are indicative of only some of the various ways in which the principles of the disclosure may be employed, and the present disclosure is intended to include all such aspects and their equivalents. Other advantages and novel features of the disclosure will become apparent from the following description when considered in conjunction with the drawings.

BRIEF DESCRIPTION OF THE DRAWINGS

The disclosure can be readily understood by considering the following detailed description in conjunction with the accompanying drawings, in which:

FIG. 2 illustrates an exploded view of an embodiment of an offset wireless battery pack.

FIGS. 5A-5H illustrate various perspective, top, side, bottom, front, and rear views of an embodiment of an offset wireless battery pack.

FIGS. 8A-8G an embodiment of a needling machine offset battery pack kit featuring perspective, front, back, side, top, and bottom views.

FIGS. 10A-10G illustrate an embodiment of a needling machine offset battery pack kit featuring perspective, front, back, side, top, and bottom views.

FIGS. 11A-11G illustrate an embodiment of a needling machine offset battery pack kit featuring perspective, front, back side, top, and bottom views.

DETAILED DESCRIPTION

Figure 1A:
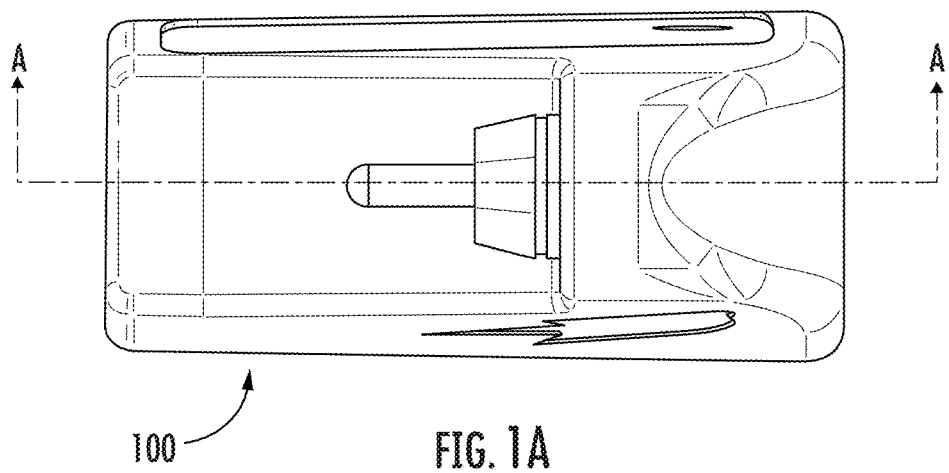
FIG. 1A illustrates a top view of an embodiment of an offset wireless battery pack.

The following detailed description and the appended drawings describe and illustrate various embodiments of the disclosure for the purpose of enabling one of ordinary skill in the relevant art to make and use the disclosure. As such, the detailed description and illustration of these embodiments are purely exemplary in nature and are in no way intended to limit the scope of the disclosure, or its protection, in any manner. It should also be understood that the drawings may not be to scale and in certain instances details have been omitted, which are not necessary for an understanding of the present disclosure, such as conventional details of fabrication and assembly.

In the Summary above, in the Description, and in the accompanying drawings, reference is made to particular features of the disclosure. It is to be understood that the disclosure in this specification includes various possible combinations of such particular features. For example, where a particular feature is disclosed in the context of a particular aspect or embodiment of the disclosure, or a particular claim, that feature can also be used, to the extent possible, in combination with and/or in the context of other particular aspects and embodiments of the disclosure, and in the disclosure generally.

The term "comprises" and grammatical equivalents thereof may be used herein to mean that other components, structures, steps, etc. are optionally present. For example, an article "comprising" (or "which comprises") components A, B, and C can consist of (i.e., contain only) components A, B, and C, or can contain not only components A, B, and C, but also one or more other components or structures.

Unless otherwise specified, the terms "approximately" and "about" when used in the context of a numeric figure may be defined to mean±20% of the corresponding number(s). The term "at least" followed by a number may be used herein to denote the start of a range beginning with that number (which may be a range having an upper limit or no upper limit, depending on the variable being defined). For example, "at least 1" means 1 or more than 1. The term "at most" followed by a number may be used herein to denote the end of a range ending with that number (which may be a range having 1 or 0 as its lower limit, or a range having no lower limit, depending upon the variable being defined). For example, "at most 4" means 4 or less than 4. When, in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm, and whose upper limit is 100 mm.

While the specification will conclude with claims defining the features of embodiments of the disclosure that are regarded as novel, it is believed that the disclosure will be better understood from a consideration of the following description in conjunction with the figures, in which like reference numerals are carried forward.

One embodiment of an offset wireless battery pack device, in accordance with the disclosure, includes one or more battery cells, a machine power interface, a charging interface, electronic circuitry, and a housing. The housing may have a main body portion and a machine mating portion. The machine body portion may be dimensioned to contain one or more battery cells in the electronic circuitry, while the machine mating portion is positioned on a machine-facing side of the main body portion so that when the offset wireless battery pack is mated to a needling machine, it is offset the distance from the needling machine. The electronic circuitry is electrically connected to the one or more battery cells, the machine power interface, the machine charging interface, and also may include a power controller, a processor, a memory, an input button, and/or a light emitting diode (LED).

In some embodiments, the electronic circuitry may also include a wireless transceiver, a wireless chip, a communications module, a radio, or a combination thereof.

With respect to the power controller, some embodiments may include controlling voltage delivered to the machine power interface incrementally over a range. In certain embodiments, the voltage increment may be about 0.5 volts, and the range may be from zero volts to about 12 volts. Another range may be from about 4.5 volts to about 12.0 volts. Other suitable voltage increments and/or ranges may also be utilized as desired.

In certain embodiments, the offset wireless battery pack may include an LED capable of emitting a variety of wavelengths of visible light. In certain embodiments, specific wavelengths of light may correspond to specific incremental voltages output by the offset wireless battery pack. In certain embodiments, the offset wireless battery pack may include a display screen that may be used to display a range of information, including, but not limited to, battery status information, battery charging status information, information associated with a tattoo recipient (e.g. the name, physical statistics, preferences, and/or demographics of a tattoo recipient currently receiving a tattoo during a tattoo session), voltage information (e.g. the current voltage setting for the tattoo machine), whether the battery pack is paired with another device, a communication capability, parameters associated with the tattoo machine that may be adjusted and/or retrieved using the tattoo machine (e.g. brightness levels of the display, an amount of delivered current, sensor data (e.g. temperature of the tattoo machine, humidity levels, motor status information (e.g. whether the motor is operating or not), any other information, or a combination thereof. In certain embodiments, the display may be a LCD display, OLED display, plasma display, retina display, touchscreen display, and/or any type of display.

In still another embodiment, a wireless needling machine kit is disclosed, which may include a needling machine having a cartridge end, an input end, and an exterior machine profile therebetween. The kit may also include an offset wireless battery pack which may include a machine mating portion and a machine power interface. The machine power interface may be configured to electrically couple to the input end of the needling machine, while the machine mating portion may be dimensioned to correspond to and mate with a portion of the exterior machine profile. In this way, when the offset wireless battery pack is operatively connected to the needling machine, the wireless battery pack may sit substantially alongside the needling machine, cradling the contour of the needling machine and thus creating a more unified wireless needling device with an optimized massing and placement of the battery pack.

Another embodiment of an offset wireless battery pack includes one or more battery cells, a machine power interface for delivering direct current voltage to a needling machine, a charging interface, electronic circuitry, and a housing. The electronic circuitry may be contained within the housing and may be in electrical communication with the one or more battery cells, the machine power interface, and the machine charging interface. The electronic circuitry may be configured to control the voltage supplied by the one or more battery cells to the machine power interface. The housing may consist of an exterior, an interior, and a machine mating portion. The interior of the housing may be dimensioned to contain the one or more battery cells, together with the electronic circuitry, machine power interface, and the machine charging interface. The interior may define a main body portion which has a center of mass. The machine mating portion of the housing may be positioned a distance from the center of mass of the main body portion such that the center of mass is offset a distance from a needling machine when the offset wireless battery pack is mated to the needling machine.

A further embodiment of the present disclosure includes a method of using an offset wireless battery pack device.

Another embodiment of the present disclosure includes a method of using an offset wireless battery pack device comprising providing a needling machine, providing an offset wireless battery pack, providing a needling substrate, such as a person, animal, or leather, connecting the offset wireless battery pack to the needling machine, and operating the needling machine upon the needling substrate.

Still further embodiments of the present disclosure include a method of using an offset wireless battery pack device comprising providing a needling machine, providing one or more offset wireless battery packs, each pack having one or more voltage settings, providing a needling substrate, connecting the offset wireless battery pack to the needling machine, selecting a voltage setting on the offset wireless battery pack in order to operate the needling machine, and operating the needling machine upon the needling substrate.

Still further embodiments of the present disclosure include methods of applying ink to skin. The method may include providing a needling skin substrate, providing a needling machine, providing a needle cartridge having one or more needles, providing an ink, providing an offset wireless battery pack, operatively connecting the offset wireless battery pack to the needling machine, operatively connecting the needling cartridge to the needling machine, setting a voltage on the offset wireless battery pack in order to operate the needling machine to which it is connected, dipping the tip of the one or more needles in the ink, and applying the tip of the one or more needles to the needling skin substrate. Optionally, the method may include providing a rinse solution and rinsing the one or more needles in the rinse solution. Other embodiments may include providing a second color ink, rinsing the one or more needles in the rinse solution, dipping the tip of the one or more needles in the second color ink, and applying the tip of the one or more needles having the second color ink to the needling substrate. Still further embodiments may include repeating the steps of rinsing, dipping, and applying steps until a complete design is achieved upon the needling substrate.

The offset wireless battery pack housing may be configured to allow the pack to power needling machines in such a way so as to minimize the change in the center of mass of the needle machine to the new center of mass of the combined machine and pack.

A needling machine may have a power interface defining an axis or plane, and a corresponding power interface on a power source has an axis or plane corresponding to the machine's power interface so that coupling the power source to the needling machine requires co-planar or co-axial displacement. In certain embodiments, power sources may thus engage needling devices by approaching that power interface in a particular orientation. Some needling machines have a motor housing having an approximately cylindrical shape with a central axis. The machine's power interface is frequently co-axial with that central axis.

The main body portion of the offset wireless battery pack may be configured to closely approximate and align with a side of the needling machine. The side of the needling machine may be the motor housing. By aligning the offset wireless battery pack on the side of the needling machine, the center of mass of the offset wireless battery pack is positioned longitudinally closer to the needling machine or motor housing, and radially close to the central axis of the needling machine or motor housing. In certain embodiments, the body portion may also be positioned away from the needling machine by utilizing a wire from the offset wireless battery pack to the needling machine. Additionally, in certain embodiments, the battery pack may include a detachable system to facilitate the mating of the battery pack with different types of needling machines that may utilize different power connection capabilities.

The main body portion of the offset wireless battery pack may be positioned to the side relative to the needling machine or its motor housing. To electrically couple with the rear end of the motor housing, the machine power interface on the battery pack may be positioned on one side of the offset wireless battery pack, rather than the top or bottom of the pack, and optimally rearward of the battery pack's center of mass. The configuration of the offset wireless battery pack thus minimizes the overall length of the combined machine and pack when measured from machine needle tip end to the back of the battery pack. In this way, the battery pack minimizes the increase in angular torque resulting on a user's hands when the battery pack is attached operatively to the needling machine.

Power interfaces on needling machines may vary. In some embodiments, the offset wireless battery pack power interface may be a male RCA adapter. In certain embodiments, the adapter may be a male USB-C adapter, a ¼" power jack connector, male 3.5 mm adapter, other adapter, or other means for low voltage direct current power from the offset wireless battery pack to the needling machine.

The power source contained within the offset wireless battery pack may comprise one or more individual battery cells. The battery pack may be configured in a variety of shapes depending on the configuration and orientation of the mechanical components of the apparatus.

Electrical circuitry within the offset wireless battery pack may be configured to control delivery of power to the machine power interface. The voltage potential may be varied on demand by a power controller electrically coupled to the battery and machine power interface. A processor in the electrical circuitry in turn controls the power controller depending on pre-programmed settings contained in memory, a user's direct adjustment of the voltage through a button provided on the side of the pack housing, or wirelessly from another control source.

The voltage potential at the machine power interface may be incrementally changed by the electrical circuitry. For example, the electronic circuitry may include pre-determined voltage settings. Specific settings might include a step-wise increment of 0.1 volts over a range from zero volts up to about twelve volts. Another range of stepped voltages may range from about 3.0 volts to about 12.0 volts. Other ranges of voltages and step-wise increments may also be utilized as desired as well.

In a preferred embodiment, the electrical circuitry is configured to deliver a potential of 5.0 volts to 12.0 volts in increments of 0.5 volts. In this preferred embodiment, there are 15 different voltages delivered to the machine power interface based on a user's input.

Parameters of the offset wireless battery pack may be set by a user according to one or more buttons on the battery pack itself. Buttons on board the battery pack allow for the needling device to be operated completely independent of any other equipment, such as a wired power source, a control unit, or foot switch, although such peripheral devices may optionally wirelessly communicate with the offset wireless battery pack. Other interfaces, devices, and/or mechanisms may also be utilized to control the parameters. For example, the parameters may be controlled and/or set by utilizing voice commands from devices including, but not limited to, smart watches and/or speakers, mobile devices and/or wired and/or wireless headsets. Additionally, such parameter settings may be set and/or controlled by using keypads on displays, such as, but not limited to, capacitive touch surfaces.

In a preferred embodiment, an offset wireless battery pack may include three buttons. The first button may increase the voltage. A second button may decrease the voltage. A third button may turn power delivery to the machine power interface on and off, thus indirectly controlling the power state of the needling machine.

An offset wireless battery pack may also include a LED or other light source to provide a user with visual feedback on the various states of the battery pack. States of the offset wireless battery pack may include, but are not limited to, its current (i.e. present-time) voltage setting, the amount of battery life remaining, an amount of time to recharge the battery cells of the battery pack, or a combination thereof. In certain embodiments, a single LED may be provided on the exterior of the housing, which may be capable of producing a plurality of colors. Various colors of the LED may correspond to pre-defined voltage settings, such that when the user selects particular voltage on the wireless tattoo machine, the LED may emit a continuous source of a specific color, or flashes. The particular color and its corresponding voltage may be shown on a legend printed onto the wireless battery pack. Various colors and flash combinations may represent different voltage settings. Similarly, different colors and sequence of flashes may provide a user with other information about the wireless tattoo machine. By way of example and not limitation, a constant red-color light emitted from the LED may indicate a completely drained battery. Another state may include a green flashing LED at a rate of flashing different from the flashing green light associated with a voltage setting. Such fast-paced green flashing LED may indicate a near-full charge of the battery. In certain embodiments, the LED may have a yellow-color light emitted when the charge of the battery is approximately mid-charge (e.g. 40%-60% charge). Additionally, the use of a digital display, such as an LCD screen, OLED screen, touchscreen, and/or other screen, may be used to communicate information as described herein in addition to other options to display additional information such as client and session data.

The offset wireless battery pack circuitry may also include electrical safety features. Such safety features may include overcurrent protection to prevent the flow of electricity from the battery to the motor under certain conditions. Such overcurrent protection may be triggered when the motor has completely failed, seized, and/or is in the initial stages of failure. Overcurrent protection may also be triggered when a motor bearing has failed or has reached a sufficient level of frictional resistance impeding the rotation of the motor. In certain embodiments, if the motor is no longer seizing, has been repaired, or is no longer in a stage of failure, the circuitry may restart the flow of electricity from the battery to the motor.

In certain embodiments, the offset wireless battery pack may include one or more transceivers to wirelessly communicate with other devices. In certain embodiments, the offset wireless battery pack may include one or more wireless chips, communications modules, radios, and/or other components for communicating with devices remote from the needling machine and/or battery pack. In further embodiments, other devices may be configured to specify the operational parameters of the battery pack and the power delivered to the needling machine. In some embodiments, the wireless device may be a foot switch. In other embodiments, the wireless device may be a cellular phone, tablet, phablet, mobile device, computer, smartwatch, smart speaker, server, earbud, other computing device, a wireless robot, or a combination thereof. In still other embodiments, the wireless device capable of communicating with the offset wireless battery pack may be a needling device control unit. In this way, the needling machine may be controlled wirelessly by the peripheral devices.

Methods of using an offset wireless battery pack device are also disclosed. An offset wireless battery pack may be provided, together with a needling machine. The battery pack may be operatively engaged and attached to the needling machine, such that the needling machine is thereby powered by the battery pack. The battery pack may have controls directly on its exterior and the settings of the battery pack may be specified by a user. Visual feedback of a state of the battery pack may be provided to a user visually from a light source or a digital display, such as an LCD or other screen, on board the wireless battery pack. A needling substrate may be provided, such as human skin, animal skin, leather, and/or any number of other substrates capable of resiliently accepting repeated puncturing by a needle or microneedle. The combined machine and battery pack may be operated upon the needling substrate to deliver inks, therapeutic compounds, or simply for innate stimulation of the substrate itself.

Methods of using one or more offset wireless battery packs are also disclosed. A first offset wireless battery pack and a second offset wireless battery pack may be provided. The first offset wireless battery pack may be operatively coupled to the needling machine and operated upon a needling substrate until the first offset wireless battery pack is depleted. The first battery pack may then be removed, and the second offset wireless battery pack may be operatively coupled to the needling machine, thus allowing uninterrupted needling of the substrate. The offset wireless battery pack not then currently in use may be charged. In this way, two (or any desired number) battery packs may be continuously cycled between use and charging without requiring a user to discontinue a needling session.

Figure 1B:
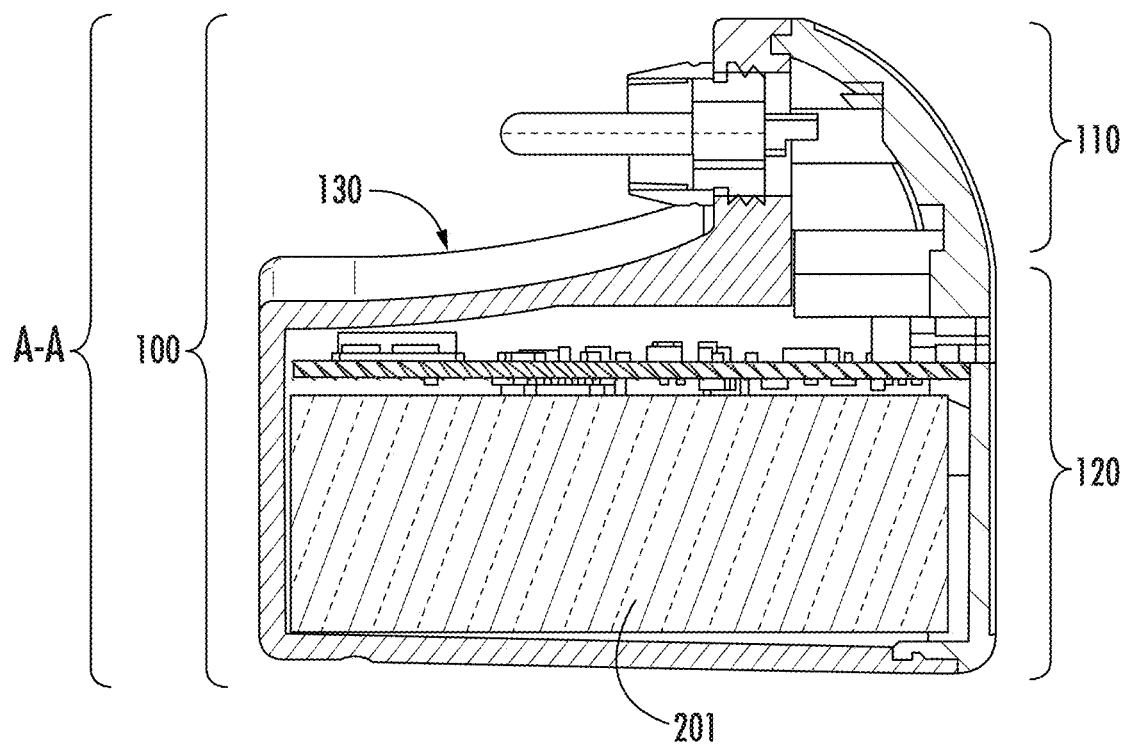
FIG. 1B illustrates a side cross-sectional view of an embodiment of an offset wireless battery pack.

Now, with reference to FIGS. 1A-1B, a top view and a cross-sectional view of an embodiment of the offset wireless battery pack 100 is provided in accordance with the disclosure. The battery pack housing of the offset wireless battery pack 100 includes an offset machine-facing interface portion 110, and a main body portion 120. In certain embodiments, a battery 201 is contained within the main body portion 120. Notably, any number of batteries 201 may be contained within the main body portion 120 depending on the desired amount of power for powering a tattoo or needling machine to be powered by the offset wireless battery pack. Electronic circuitry is also included within the main body portion 120. Positioned between the offset machine-facing interface portion 110 and the main body portion 120 is a contoured portion or housing face 130. The contoured portion 130 is dimensioned and configured to correspond to a portion of a needling machine exterior. For example, the contoured portion or housing face 130 can provide a convex surface and can also have curved side edges on opposite sides of the convex surface. The curved side edges and entire contoured portion or housing face 130 can be curved towards proximal and slope away in the opposite direction towards the distal end of the contoured portion or housing face 130. For example, the portion of the needling machine exterior may glide onto the contoured portion 130 so that the portion of the needling machine exterior may readily engage with and secure onto the offset machine-facing interface portion 110.

Turning now also to FIG. 2, an exploded view of an embodiment of the offset wireless battery pack is provided. The machine power interface of the offset wireless battery pack may include a male RCA connector 203A. In certain embodiments, the RCA connector 203A may be positioned on any side and/or location of the offset wireless battery pack. The RCA connector 203A can extend parallel to and along the length of at least a portion of the main body housing 120. Such flexibility may allow for different attachment configurations when the offset wireless battery pack is attached to a tattoo machine. A charging interface separate from the machine power interface is provided in the form of a female USB-C adapter 202A. A printed circuit board supports and provides the electrical conductivity between the various components comprising the electronic circuitry 200 and battery 201. The offset wireless battery pack may also include a component 204, which may be utilized to secure the main body portion 120 and the machine-facing interface portion 110 together. In certain embodiments, a charging port for charging the battery 201 of the offset wireless battery pack may be included within the component 204 as well.

Figure 3:
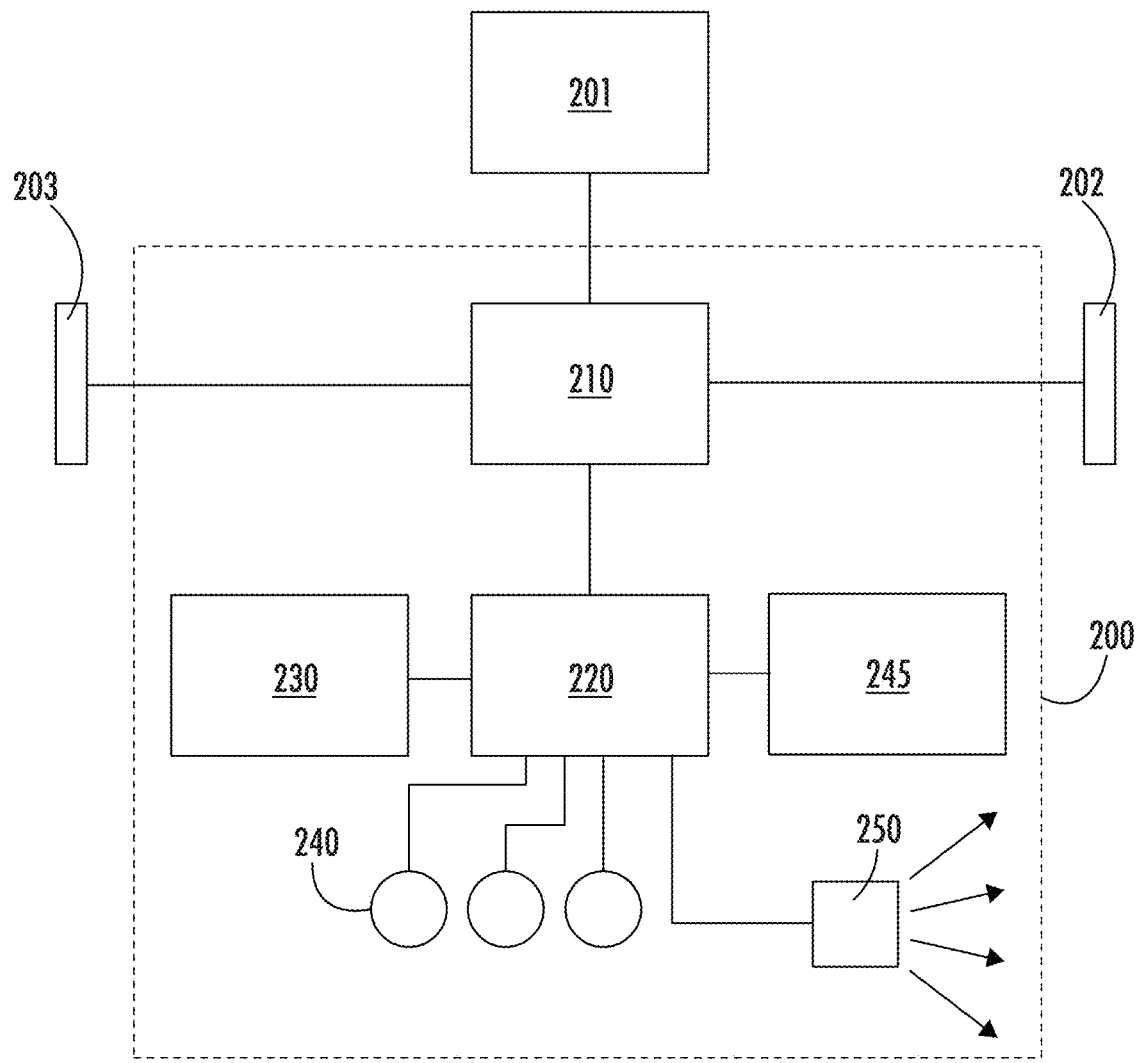
FIG. 3 illustrates a schematic of electrical components contained within an embodiment of an offset wireless battery pack.

FIG. 3 shows the configuration of the electrical components in an embodiment of the offset wireless battery pack. Electronic circuitry 200 off the offset wireless battery pack may include, but is not limited to including, a power controller 210, a processor 220, a memory 230, buttons 240, a communications component 245, and/or an LED/LCD/OLED display 250. The power controller 210 may be utilized to regulate the flow of electricity to various components of the offset wireless battery pack, such as, but not limited to, the charging interface 202, the power interface 203, any other components of the wireless battery pack, any components of a needling machine secured to the offset wireless battery pack, or a combination thereof. The processor 220 of the offset wireless battery pack may be hardware, software, or a combination of hardware and software. The processor 220 may be configured to execute various operations of the offset wireless battery pack based on instructions stored in the memory 230, based on receiving inputs via the buttons 240, and/or based on receiving signals from remote devices communicatively coupled to the offset wireless battery pack. Such signals may be received by a communications component of the offset wireless battery pack, such as by a communications component 245 (e.g. transceiver) of the offset wireless battery pack. The memory 230 may be also be hardware, software, or a combination of hardware and software. In certain embodiments, the memory 230 may be configured to store instructions, which the processor 220 may be configured to execute so as to perform various operations of the offset wireless battery pack. Additionally, the memory 230 may also be configured to store data and signals received from devices communicatively coupled to the offset wireless battery packs (e.g. from devices controlling the offset wireless battery pack and/or needling machine connected thereto), voltage settings of the offset wireless battery pack, information associated with patterns of usage of the offset wireless battery pack, information identifying users of the offset wireless battery pack and/or needling machines connected thereto, battery life information for the battery 201, any other information, or a combination thereof.

The electronic circuitry 200 of the offset wireless battery pack may be in electrical communication with a battery cell 201, machine power interface 203, the processor 220, the memory 230, the buttons 240, the communications component 245, the LED/LCD 250, and charging interface 202. User input signals generated by interactions with buttons 240 may be processed by processor 220. Such input signals may set and/or indicate voltage settings for the offset wireless battery pack, whether to prevent power from being delivered to the machine power interface 203, whether to deliver power to the machine power interface 203, whether to delivery electricity to the battery 201 via the charging interface 202, any other input signals, or a combination thereof. In certain embodiments, other settings and/or status information may also be indicated by the input signals including, but not limited to, battery charging status information, battery level information, tattoo machine temperature information, needle reciprocation information, tattoo session time information, tattoo progress information, any other information, or a combination thereof. In certain embodiments, for example, the processor 220 may provide a signal to the power controller 210, and the power controller 210, in turn, may regulate the flow of electricity from the battery 201 to machine power interface 203. Power controller 210 may also control delivery of electricity supplied through charging interface 202 to battery 201, to machine power interface 203, or both simultaneously charge battery 201 while also providing power to the machine power interface 203. LED/LCD/OLED 250 may provide visual feedback to a user about a status of settings contained within electronic circuitry 220, a status of battery 201, a status of charging or power provided by the charging interface 202, other parameters as configured by the processor 220 and stored in memory 230, and/or parameters delivered to the tattoo machine from a remote system, such as via the communications component 245.

In certain embodiments, the communications component 245 may be a wireless chip, a radio, a communications module, a transceiver, a cellular chip, any type of communications component, or a combination thereof. In certain embodiments, the communications component 245 may be utilized to facilitate communications between the offset wireless battery pack (e.g. offset wireless battery pack 100 and/or other battery packs disclosed herein) and any number of other devices. In certain embodiments, the communications component 245 may communicate with devices that may be utilized to control one or more components of the offset wireless battery pack. For example, a foot switch, a mobile device (e.g. smartwatch, cell phone, tablet, laptop, etc.), and/or a computer may communicate with the communications component 245 and transmit signals including inputs for controlling the offset wireless battery pack componentry. In certain embodiments, a control device may transmit signals to the offset wireless battery pack including inputs for specifying voltage settings of the offset wireless battery pack, an amount of voltage to deliver to the componentry of the offset wireless battery pack, an amount of power to be made available to the power interface 203 for powering a needling machine coupled to the offset wireless battery pack, whether to activate or deactivate the offset wireless battery pack and/or needling machine, settings for reprogramming the functionality associated with each of the buttons 240, and/or adding and/or specifying operations for the processor 220 to perform.

In certain embodiments, devices communicatively linked to the communications component 245 may transmit data to the offset wireless battery pack to store in the memory 230 and/or to process using the processor 220. For example, a device may transmit a user profile including information associated with a user of offset wireless battery pack and/or needling machine mated with the offset wireless battery pack. The user profile may include any information associated with the user, such as, but not limited to, the user's name, demographic information, physical metrics, preferences associated with use of the offset wireless battery pack and/or needling machine, voltage setting preferences, color preferences for the LEDs 250, preferences for the functionality of the buttons 240, any other information, or a combination thereof. In certain embodiments, the information specified in the user profile may be analyzed by the processor 220 to automatically change the settings and/or functionality of the offset wireless battery pack and/or needling machine in accordance with the information in the user profile. For example, the user profile may specify a specific voltage that the user wishes to provide to the power interface 203, the specific functions associated with the buttons 240, the specific colors of the LEDs 250 (e.g. green for full power, yellow for half power, red for depleted battery or near depletion), a manner in which the processor 220 is to control the power controller 210, specific voltage settings based on the type of needling machine attached to the offset wireless battery pack, any other settings, or a combination thereof. As the user of the offset wireless battery pack and/or needling machine changes, a corresponding user profile of the new user may be loaded into the memory 230 and the settings associated with the new user may automatically update the functionality and settings of the offset wireless battery pack and/or needling machine.

In certain embodiments, in addition to user profiles, devices communicatively linked to the offset wireless battery pack may transmit device profiles for configuring the functionality of the offset wireless battery pack to operate in an optimal manner with a particular needling machine to be attached to the offset wireless battery pack. In certain embodiments, a different device profile may be created for each different type of needling machine that may be attached to the offset wireless battery pack. In certain embodiments, the device profile may specify the default voltage settings of the offset wireless battery pack for use with a particular needling machine, the default voltage range for peak performance of the needling machine with the offset wireless battery pack, a user's preferences with regard to the specific needling machine and/or offset wireless battery pack, and/or any other device-related information. User preferences may include, but are not limited to, different voltage settings than default voltage settings, different voltage ranges than default voltage ranges, what functions are to be associated with the buttons 240, and/or any other preferences. As new needling machines are secured and attached to the offset wireless battery pack, a new device profile corresponding to each new needling machine may be loaded and the corresponding settings may be automatically set by the processor 220 of the offset wireless battery pack.

Figure 4A:
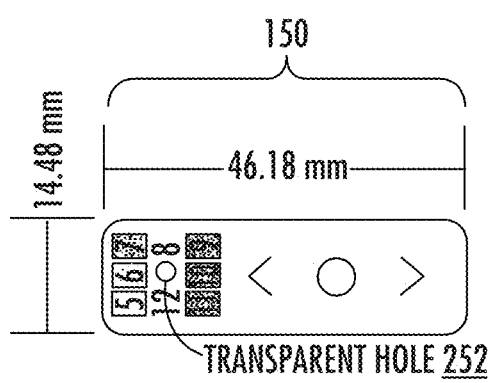
FIGS. 4A and 4B illustrate a schematic of a portion of the electrical components divided on the interior and exterior of an embodiment of an offset wireless battery pack.
Figure 4B:
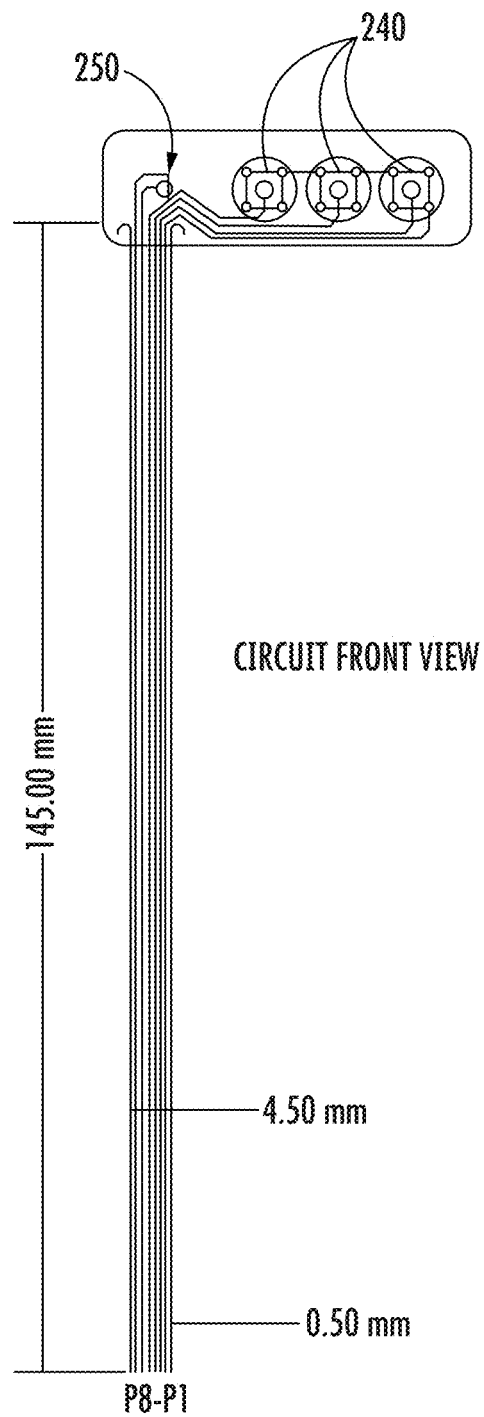

FIGS. 4A-4B provides a schematic of a portion of the printed circuitry that includes buttons 240 and LED 250 (or LCD or OLED) of an offset wireless battery pack. Overlaying that circuitry is user interface 150 specifying pre-defined colors corresponding to voltages supplied by the offset wireless battery pack to a needling machine. A transparent hole 252 is provided in the user interface 150 to allow light emitted by LED 250 to be seen by a user. Buttons 240 may be assigned to increase voltage, toggle power on and off, and decrease the voltage setting.

With regard to FIGS. 5A-5H, various views of an offset wireless battery pack are provided in accordance with the disclosure. Contoured portion 130 can be seen from a variety of perspectives demonstrating the contoured portion 130 of the offset wireless battery pack that corresponds to and engages with the exterior contours of a needling or tattoo machine. Male RCA connector 203A (or other suitable connector) is positioned offset from the main body portion of the pack and oriented to allow the offset wireless battery pack to mate with and secure to a needling machine so that, when coupled, the contoured portion 130 approximately closely follows the contours of a needling machine when the machine power interface male RCA connector 203A is mated with the corresponding female RCA connector on the needling machine. Aperture 251 is provided on a side of the housing to allow a portion of the electronic circuitry to be accessible to a user, such as a button. A female USB-C 202A charging interface (or other suitable charging interface) is also provided on the top portion of the machine, oriented rearwardly from the needling machine. In certain embodiments, an end of a charging cord may be plugged into the female USB-C 202A charging interface and the other end of the charging cord may be plugged into an electrical socket so as to deliver electricity to the battery 201 of the offset wireless battery pack.

Figure 6D:
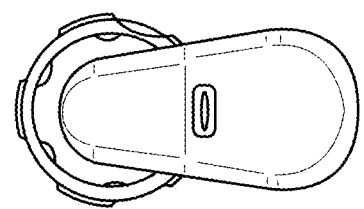
FIGS. 6A-6D illustrate an embodiment of a needling machine offset battery pack kit featuring side, front, and back views.
Figure 6A:
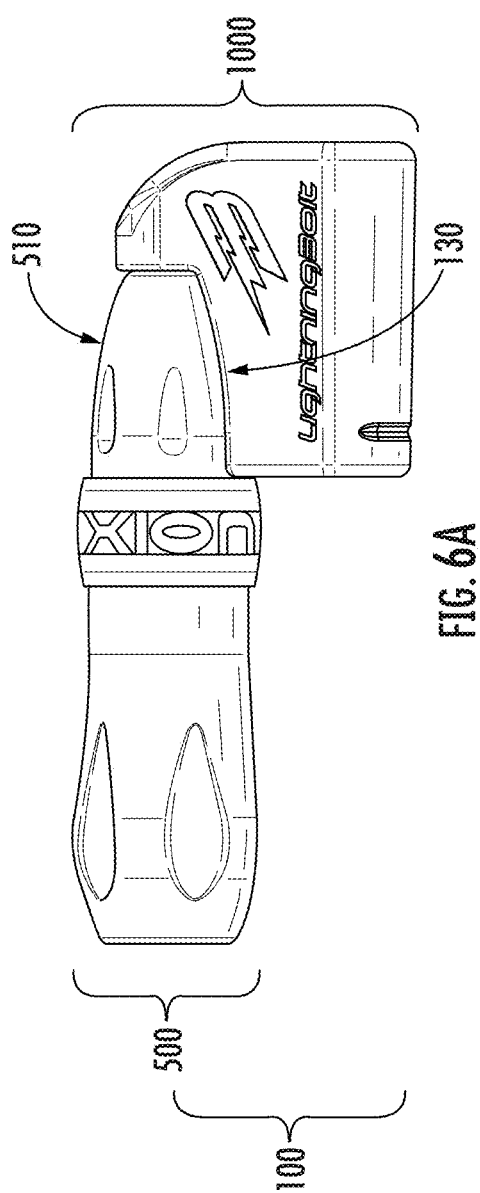
Figure 6C:
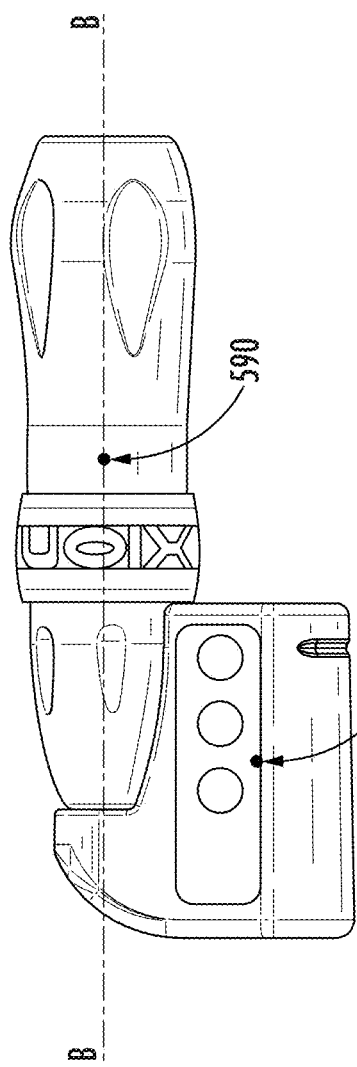
Figure 6B:
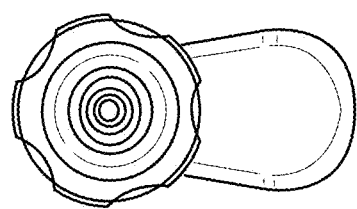
Figure 7:
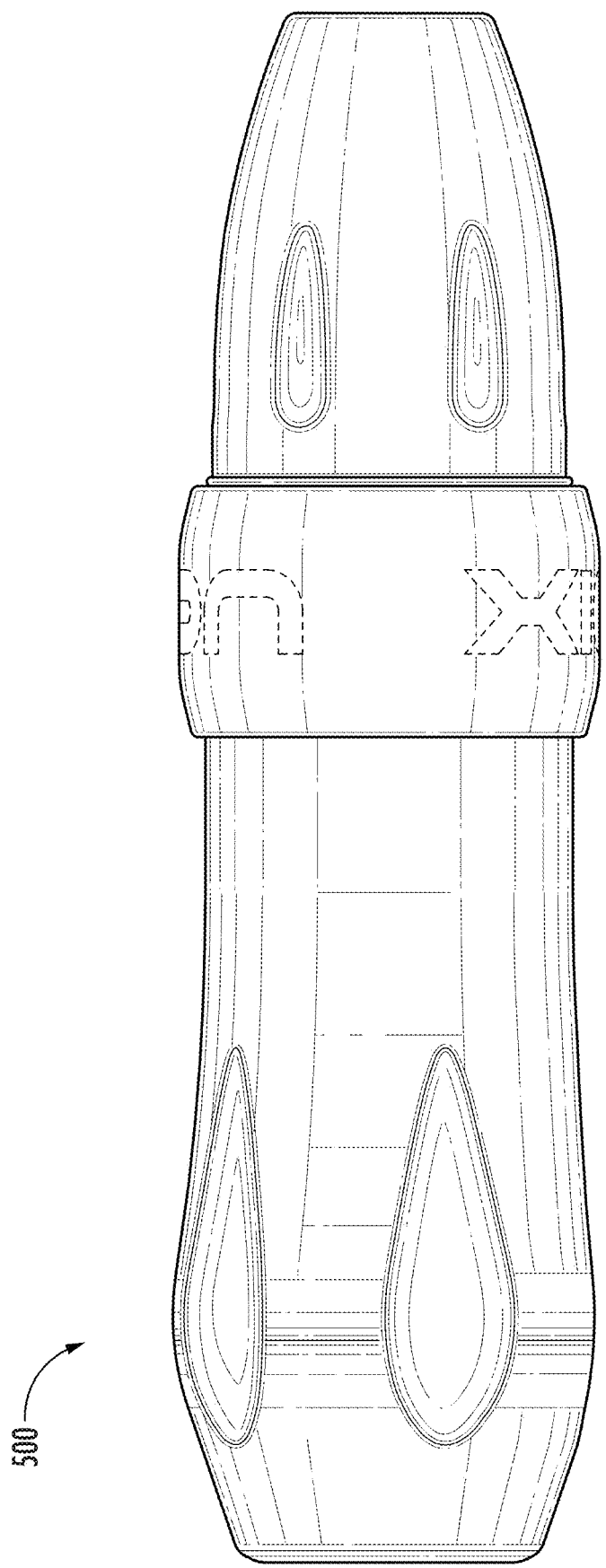
FIG. 7 illustrates an embodiment of a needling machine.

In the embodiment shown at FIGS. 6A-6C, the offset wireless battery pack 100 is shown extending along and offset from a longitudinal length of the needling machine 500. When the offset wireless battery pack 100 is attached to the needling machine 500 as shown in FIGS. 6A-6C, the center of mass of the offset wireless battery pack 100 is located distal to the region of attachment of the offset wireless battery pack 100 and the tattoo or needling machine 500 and along the longitudinal length of the needling machine 500. In this regard, when the offset wireless battery pack 100 is attached to the needling machine 500, the center of mass of the offset wireless battery pack 100 is located between the work end, where a needle is provided, and the power end, to which the offset wireless battery pack 100 attaches. Additionally, the RCA connector 203A of the offset wireless battery pack 100 is colinear with the central longitudinal axis of the needling machine 500. In this arrangement, the length of the housing of the offset wireless battery pack 100 is parallel to the central longitudinal axis of the needling machine 500 and offset from it a distance at least as long as the diameter of the exterior of the RCA connector 203A.

Further, when the offset wireless battery pack 100 is attached to the needling machine 500, the combined center of mass of the offset wireless battery pack 100 and the needling machine 500 is located distal to the region of attachment of the offset wireless battery pack and the needling machine and along the longitudinal length of the needling machine. In this regard, when the offset wireless battery pack 100 is attached to the needling machine 500, the combined center of mass of the offset wireless battery pack 100 and the needling machine 500 is located between the work end, where a needle is provided, and the power end, to which the offset wireless battery pack attaches.

Now with reference to FIGS. 6A-6C and 7, an embodiment of a kit including an offset wireless battery pack 100 and needling machine 500 is provided in accordance with the disclosure. Offset wireless battery pack 100 is shown operably coupled to needling machine 500 in machine-pack kit combination 1000. The contoured portion 130 of the offset wireless battery pack 100 sits alongside a portion of exterior machine profile 510, and the portion of exterior machine profile 510 engages with RCA connector 203A of the offset wireless battery pack 100. Needling machine 500 has, independent of any power source, a central axis B-B, and a center of mass 590. Offset wireless battery pack 100 has, independent of any needling machine, a center of mass 190. The centers of mass illustrated in FIGS. 6A-6C and 7 are approximate, and may not depict the exact actual location of their respective centers of mass. Instead, the centers of mass are shown to demonstrate their approximate proximity to one another as a result of the configuration of the offset wireless battery pack.

Turning to FIGS. 8A-8G, various views of an embodiment of a kit including an offset wireless battery pack 800 and tattoo or needling machine 810 are provided. The needling machine 810 of FIGS. 8A-8G may be configured to have a different shape and center of mass than needling machine 500, and may provide a user with a different option for conducting tattooing, microneedling, and/or therapeutic sessions on a substrate, such as a user's skin.

Figure 9:
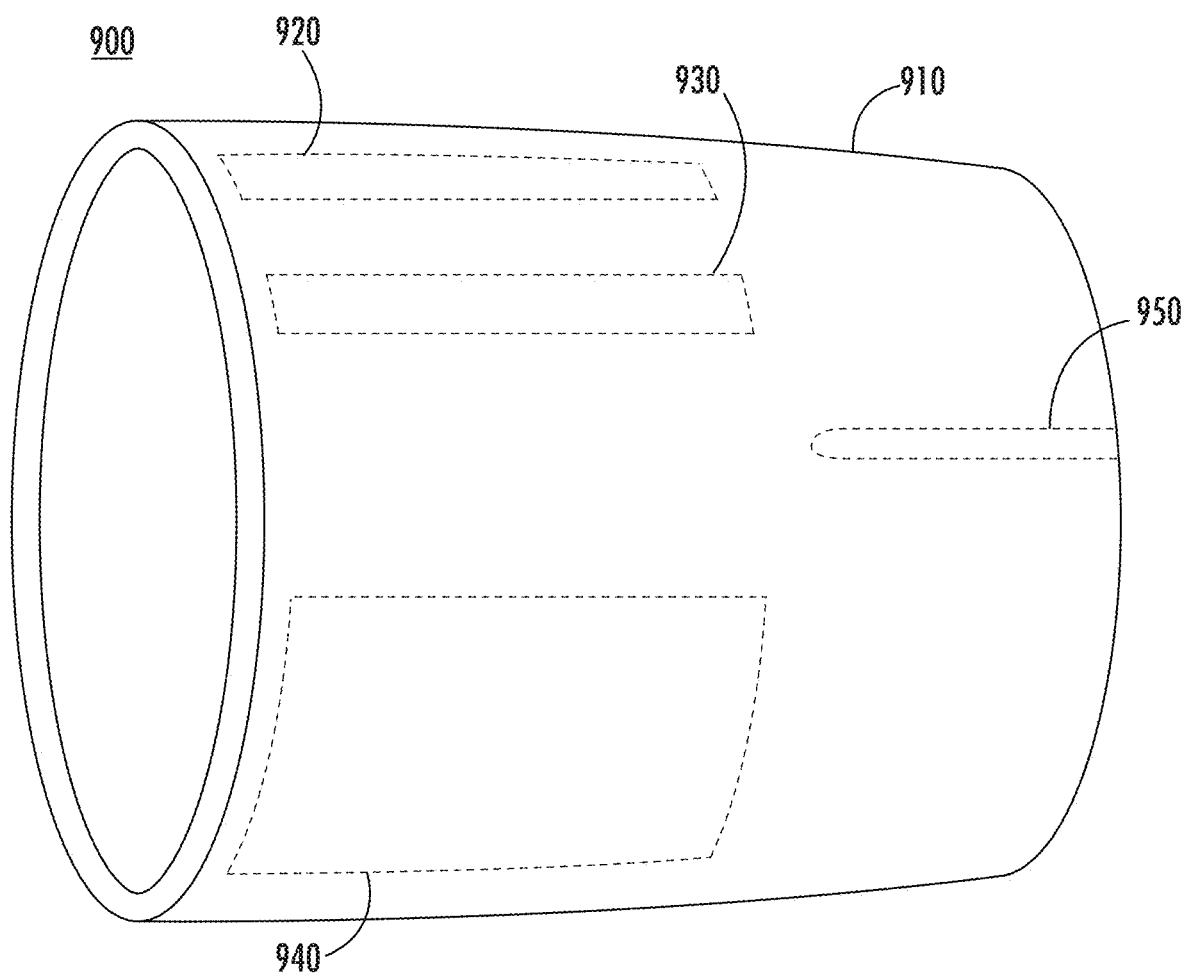
FIG. 9 illustrates another embodiment of a battery pack.

FIG. 9 illustrates another embodiment of a battery pack 900. The battery pack 900 is shown with internal components in dotted lines. The battery pack 900 can include a housing 910 and one or more batteries 920, 930 and 940. In certain embodiments, the batteries 920 and 930 may be cylindrical batteries and the housing 910 may include a plurality of such batteries. Alternatively, or in addition to multiple cylindrical batteries 920 and 930, the battery pack 900 may include a circular shaped battery 940 that encircles the entirety or a portion of the housing 910. An electrical contact 950 may also be provided with the battery pack 900 to provide an electrical connection and/or control signals to a needling machine attached to the battery pack 900. In certain embodiments, the electrical connection may reside completely within the housing 910 without any portion extending away from the housing 910. In certain embodiments, the battery pack 900 may include a charging port, which may be configured to couple to charging cord so as to recharge any one or more of the batteries 920, 930, and 940. In certain embodiments, the battery pack 900 may include an interface on a surface of the battery pack 900, which may display status information associated with each of the batteries 920, 930, and 940. For example, the status information may include, but is not limited to, a remaining battery life for each of the batteries 920, 930, 940, whether a needling machine is attached to the battery pack 900, an amount of power being delivered to a needling machine, whether a battery 920, 930, 940 has depleted, whether the charging cord is connected to the charging port, whether the battery pack 900 is delivering power to a needling machine, whether a needling machine attached to the battery pack 900 is in use or in stand-by mode, any other status information, or a combination thereof.

In certain embodiments, the location of the one or more batteries 920, 930 and 940 can provide a concentric or at least generally uniform weight distribution around the central axis of the battery pack 900 such that no portion of the battery pack 900 is substantially heavier than the another portion of the battery pack 900. Such a weight distribution will provide a center of mass that is generally evenly distributed around the needling machine when the battery pack 900 is placed over the needling machine. Additionally, the location of the one or more batteries 920, 930 and 940 at the end of the opening of the housing 910 and away from the opposite end of the housing 910 results in a center of mass of the battery pack 900 located distal to the opening of the housing 910. In such an arrangement, when the battery pack 900 is connected to a needling machine, the combined center of mass is located adjacent to the grip of the needling machine in between the work end of the needling machine and power end of the needling machine.

Turning to FIGS. 10A-10G and 11A-11G, additional embodiments of a kit including an offset wireless battery pack and needling machine are provided. For example, in FIGS. 10A-10G, an offset wireless battery pack 1050 mated with a tattoo or needling machine 1070 is schematically illustrated in various views. Similarly, in FIGS. 11A-11G, an offset wireless battery pack 1100 mated with a tattoo or needling machine 1150 is schematically illustrated in various views. Notably, depending on the type of needling machine secured to an offset wireless battery pack, the center of mass may adjust accordingly. As a result, each user can determine which needling machine and offset wireless battery pack combination is the optimal combination for that particular user. In certain embodiments, the offset wireless battery packs disclosed in the present disclosure may allow a needling machine to attach to the offset wireless packs in different orientations and configurations so as to enable a user to find the specific combination that is most comfortable for the user. As can be seen in certain of FIGS. 6A-6C, 8A-8G, 10A-10G, and 11A-11G, the battery pack may be combined with a variety of needling machines to comprise a kit. Furthermore, these alternative needling machines demonstrate the relationship of the center of mass of the machine relative to the battery pack.

As referenced in this disclosure a "needling machine" is not to be construed as a structural limitation, but is instead descriptive of the functional result of the disclosed structure. Needling describes a rectilinear motion wherein one or more needles is rapidly inserted and withdrawn from the skin of a person or animal.

In light of the foregoing description, it should be recognized that embodiments in accordance with the present disclosure can be realized in numerous configurations contemplated to be within the scope and spirit of the claims. Additionally, the description above is intended by way of example only and is not intended to limit the present disclosure in any way, except as set forth in the claims.

In addition, though the disclosure has been described in reference to several examples optionally incorporating various features, the disclosure is not to be limited to that which is described or indicated as contemplated with respect to each variation of the disclosure. Various changes may be made to the disclosure described and equivalents (whether recited herein or not included for the sake of some brevity) may be substituted without departing from the true spirit and scope of the disclosure. In addition, where a range of values is provided, it is understood that every intervening value, between the upper and lower limit of that range and any other stated or intervening value in that stated range, is encompassed within the disclosure.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present disclosure is not to be limited to the examples provided and/or the subject specification, but rather only by the scope of claim language associated with this disclosure.

What is claimed:

1. An offset wireless battery pack device comprising:
a battery;
an RCA connector for delivering a voltage supplied by the battery to a needling machine, wherein a longitudinal length of the needling machine defines a machine central longitudinal axis, wherein a needling machine grip extends along a portion of the longitudinal length of the needling machine colinear with the machine central longitudinal axis, wherein the RCA connector is colinear with the machine central longitudinal axis when the RCA connector is connected to the needling machine;
a charging interface;
electronic circuitry in electrical communication with the battery, the RCA connector, and the charging interface,
a housing having a main body portion and a machine mating portion, the main body portion dimensioned to contain the battery and the electronic circuitry, the machine mating portion positioned on a machine-facing side of the main body portion,
wherein the machine mating portion mates to an exterior of the needling machine when the RCA connector is connected to the needling machine,
wherein the main body portion is perpendicularly offset from the machine central longitudinal axis when the RCA connector is connected to the needling machine.

2. The offset wireless battery pack device of claim 1, wherein the main body portion of the housing defines a housing central longitudinal axis,
wherein the housing central longitudinal axis is parallel to and perpendicular offset from the machine central longitudinal axis.

3. The offset wireless battery pack device of claim 1, wherein the power delivers the voltage to the RCA connector by a voltage increment over a voltage range.

4. The offset wireless battery pack device of claim 3, wherein the voltage increment is 0.5 volts and the voltage range is from zero volts to about 12.0 volts.

5. The offset wireless battery pack device of claim 3, wherein the voltage increment is 0.5 volts and the voltage range is from about 4.5 volts to about 12.0 volts.

6. The offset wireless battery pack device of claim 3, wherein the voltage increment is 0.5 volts and the voltage range is from about 4.5 volts to about 12.0 volts, wherein a light emitting diode is capable of emitting multiple wavelengths of visible light.

7. The offset wireless battery pack device of claim 6, wherein the voltage increment corresponds to a specific wavelength of light emitted by the light emitting diode.

8. The offset wireless battery pack device of claim 7, wherein each voltage increment has a unique wavelength of light emitted by the light emitting diode.

9. The device of claim 1, wherein the RCA connector extends parallel with the machine central longitudinal axis when the RCA connector is connected to the needling machine.

10. The device of claim 1, wherein a combined center of mass of the offset wireless battery pack and the needling machine is located distally to the RCA connector and the needling machine and along the longitudinal length of the needling machine when the RCA connector is connected to the needling machine.

11. An offset wireless battery pack comprising:
a battery;
RCA connector for delivering a voltage supplied by the battery to a needling machine, wherein a longitudinal length of the needling machine defines a machine central longitudinal axis, wherein a needling machine grip extends along a portion of the longitudinal length of the needling machine colinear with the machine central longitudinal axis; and a housing comprising a main body portion, wherein the main body portion is configured to contain the battery, whereby the RCA connector is colinear with the machine central longitudinal axis and perpendicularly offset from the main body portion such that the main body portion is perpendicularly offset from the machine central longitudinal axis by a distance from the needling machine when the needling machine is coupled to the RCA connector.

12. The device of claim 11, wherein a combined center of mass of the offset wireless battery pack and the needling machine is located distally to the RCA connector and the needling machine and along the longitudinal length of the needling machine when the RCA connector is connected to the needling machine.

\* \* \* \* \*